United States Patent [19]

Hanson

[11] Patent Number: 5,216,161

[45] Date of Patent: Jun. 1, 1993

[54] PROCESS FOR PREPARING 2,5-DIAMINO-4,6-DICHLOROPYRIMIDINE

[75] Inventor: John C. Hanson, Betchworth, England

[73] Assignee: Beecham Group p.l.c., England

[21] Appl. No.: 820,890

[22] PCT Filed: Jul. 19, 1990

[86] PCT No.: PCT/GB90/01109

§ 371 Date: Jan. 16, 1992

§ 102(e) Date: Jan. 16, 1992

[87] PCT Pub. No.: WO91/01310

PCT Pub. Date: Feb. 7, 1991

[30] Foreign Application Priority Data

Jul. 21, 1989 [GB] United Kingdom ............... 8916698

[51] Int. Cl.$^5$ ............................................ C07D 239/48
[52] U.S. Cl. .................................... 544/330; 544/322
[58] Field of Search ............................... 544/322, 330

[56] References Cited

PUBLICATIONS

Legraverend, M. et al., "A New Route to 2,5 Diamino-4,6-dichloropyrimidine, A Key Precursor of 9-Substituted Guanines", *Synthesis*, 587–589 (1990).

C.A. 89:2153472s; Abstract of Temple, C., Jr. et al., "Preparation of 2,5 diamino-4,6-dichloropyrimidine via N-(4,6-dichloro-5-nitropyrimidin-2-yl)acetamide: The Preparation of 2-aminopyrimidine intermediates"; *Nucleic Acid Chem.* 1978, 1, 47–52.

*Primary Examiner*—John M. Ford
*Attorney, Agent, or Firm*—Yuriy P. Stercho; Stuart R. Suter; Edward T. Lentz

[57] ABSTRACT

A process for the preparation of 2,5-diamino-4,6-dichloropyrimidine, which process comprises the chlorination of 2,5-diamino-4,6-dihydroxypyrimidine with phosphorus oxychloride and a quaternary ammonium chloride or a weak tertiary amine base hydrochloride.

6 Claims, No Drawings

PROCESS FOR PREPARING 2,5-DIAMINO-4,6-DICHLOROPYRIMIDINE

This invention relates to a process for the preparation of a compound useful as an intermediate in the preparation of pharmaceutical compounds.

The compound 2,5-diamino-4,6-dichloropyrimidine of formula (I):

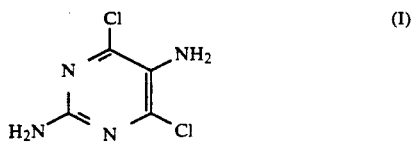

is a useful intermediate in the preparation of antiviral nucleoside analogues, such as those described in EP-A-242482 and 319228 (Beecham Group p.l.c.), and via the process described in EP-A-313289 (Beecham Group p.l.c.).

The literature reference for the preparation of this compound (Temple et. al., J. Org. Chem., 40 (21), 3141, 1975) involves a five step synthesis from 5-nitropyrimidine, giving a poor overall yield. Chlorination of 2,5-diamino-4,6-dihydroxypyrimidine of formula (II):

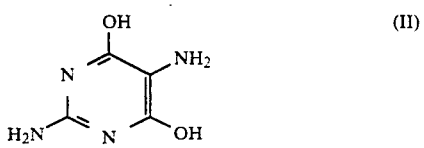

or depicted in the tautomeric form (IIA):

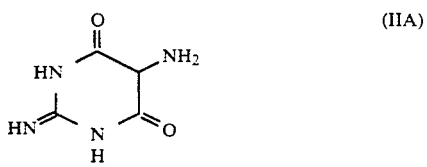

with phosphorus oxychloride is described as unsuccessful.

The literature route gives a poor yield of product which renders routes utilizing the intermediate of formula (I) commercially unfavorable.

A high yielding process has now been discovered which uses phosphorus oxychloride in the presence of a quaternary ammonium chloride as the chlorinating agents.

Accordingly, the present invention provides a process for the preparation of a compound of formula (I), as hereinbefore defined, which process comprises chlorinating a compound of formula (II), as hereinbefore defined or an acid addition salt thereof with phosphorus oxychloride and a quaternary ammonium chloride or a weak tertiary amine base hydrochloride.

The reaction is preferably carried out using the quaternary ammonium chloride as solvent, by fusing the reagents at about 100° C. The reaction may also be carried out in a polar inert organic solvent such as acetonitrile, tetrahydrofuran, dioxan, nitromethane, diglyme or dimethoxyethane, preferably acetonitrile.

Examples of ammonium substituents in a quaternary ammonium chloride include $C_{1-12}$ alkyl, usually $C_{1-4}$ alkyl, or phenyl or benzyl. Preferably a quaternary ammonium chloride is methyltriethylammonium or tetraethylammonium chloride.

Phosphorus oxychloride and a quaternary ammonium chloride are usually present in amounts of from 2-10, preferably from 3-6 molar equivalents of the compound of formula (II).

A tertiary amine weak base is, for example, N,N-dimethylaniline or diethylaniline. The base hydrochloride is usually present in an amount of approximately 2-6 molar equivalents with respect to the compound of formula (II).

The reaction is preferably carried out at an elevated temperature of from 30°-120 C., most preferably under reflux and/or with ultrasonization at around 100° C.

Preferably the reaction is allowed to proceed for a period of greater than 12 hours, usually 24-30 hours.

The above described process has the advantage that it is suitable for large scale production of the compound of formula (I).

The compound of formula (II) is prepared from 5-acetamido-2-amino-4,6-dihydroxypyrimidine, or from other corresponding 5-acyl derivatives by the action of concentrated hydrochloric acid. 5-acetamido-2-amino-4,6-dihydroxypyrimidine is prepared by condensing guanidine carbonate with diethyl 2-acetamidomalonate in ethanol or isopropanol.

The following Examples illustrate the invention. The following Description illustrates the preparation of the intermediate of formula (II).

DESCRIPTION 2,5-Diamino-4,6-dihydroxypyrimidine hydrochloride

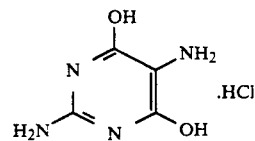

5-Acetamido-2-amino-4,6-dihydroxypyrimidine (700 g crude) (ex. guanidinium carbonate, diethyl acetamido malonate and ethanol refluxed 48 hours), concentrated hydrochloric acid (2 liters water), (200 ml), were heated to 70° and kept at 70°-75° for 1 hour, then cooled in an ice bath. The product was filtered, washed with HCl (80 ml conc HCl in water 170 ml), then acetone (1 liter), and air dried at 40° to give the title compound (344.5 g). Found: C 24.53, H 4.33, N 28.9 Cl 17.9; $C_4H_6N_4O_2 \cdot HCl \cdot H_2O$ requires C 24.4, H 4.6, N 28.5, Cl 18.0%. NMR $C^{13}$ 84.59, 115.24, 157.22 ppm DMSO MS/FAB M+H 143. Vacuum oven drying at 0.5 mm and 85° C. with argon protection gave 320 g (46% yield).

EXAMPLE 1

2,5-Diamino-4,6-dichloropyrimidine

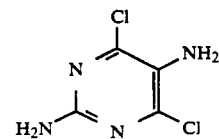

Dry Methyltriethylammonium chloride (500 g), (prepared in acetonitrile), phosphorus oxychloride (700 ml) and 2,5-diamino-4,6-dihydroxypyrimidine hydrochloride (200 g) (vacuum dried at 85° for 24 hours) were heated with stirring to 104° C. internal temperature. Hydrogen chloride gas was evolved and the reagents slowly dissolved. The reaction mixture was kept at 105° for 28 hours, cooled and the excess phosphorus oxychloride (250 ml) distilled off under vacuum up to 40° C.

The reaction mixture was poured into water (5 liters), adding ice to keep the temperature at about 50°-55° C., 40% sodium hydroxide (approximately 1100 ml) was added with ice to keep the temperature at 50°55° C., the pH adjusted to 4, and the mixture stirred for 1 hour at 50°. The pH was adjusted to 7 (40% NaOH 300 ml), cooled to 35° C. and the product was extracted with ethyl acetate (10 liters). The phases were filtered through CELITE separately to remove black solids and some phosphates. The aqueous phase was extracted with ethyl acetate (2×1 liters).

The ethyl acetate phase was washed with brine, concentrated to 4.5 liter, filtered warm through a dry silica plug (700 g 0.05 mm) to remove black solid and color, then washed through with ethyl acetate (1 liter).

The ethyl acetate was concentrated under vacuum to approximately 2 liters. The crystalline solid was filtered to yield the title compound (97.1 g). The filtrate was then concentrated to about 100 ml and filtered again to yield 34.2 g. Total yield 131 g, (65%).

A sample was chromatographed on silica and crystallized from ethyl acetate.

Found: C, 26.65, H, 2.4, N, 31.4, Cl 39.5; $C_4H_4N_4Cl_2$ requires C, 26.84, H, 2.25, N, 31.3, Cl, 39.6%.

NMR $C^{13}$ 126.04, 145.52, 154.30 ppm DMSO MS/EI 178, 180, 182, $M^+Cl_2$ pattern 143 M-Cl, 142, 115, 89, M/z, 53.

EXAMPLE 2

Dry 2,5-Diamino-4,6-dihydroxypyrimidine hydrochloride (1.8 g), tetraethyl ammonium chloride (9.8 g) (dry) and phosphorus oxychloride (5.5 ml) were heated at 105° for 20 hours. The reaction mixture was processed as in Example 1 on a smaller scale to give 0.9 g (50% yield) 2,5-diamino-4,6-dichloropyrimidine.

EXAMPLE 3

Dry 2,5-Diamino-4,6-dihydroxypyrimidine hydrochloride (3.6 g), dry N-ethyl-N-methyl piperidinium chloride (22 g) and phosphorus oxychloride (13 ml) were heated at 105° with stirring for 24 hours. The reaction mixture was processed as in Example 1 to give 2.27 g (65% yield) of 2,5-diamino-4,6-dichloropyrimidine.

EXAMPLE 4

Diethylaniline (six equivalents) was substituted for the quaternary chloride in Example 2. High pressure liquid chromatography showed the presence of 2,5-diamino-4-chloro-6-hydroxypyrimidine and 2,5-diamine-4,6-dichloropyrimidine at approximate ratio 1:1 after 20 hours.

I claim:

1. A process for the preparation of a compound of formula (I):

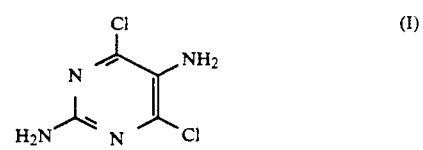

(I)

which process comprises chlorinating a compound of formula (II):

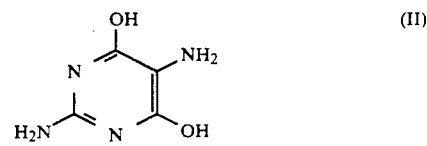

(II)

with phosphorus oxychloride and a quaternary ammonium chloride or a weak tertiary amine base hydrochloride.

2. A process according to claim 1 wherein the chlorination is with phosphorus oxychloride and a quaternary ammonium chloride.

3. A process according to claim 2, wherein the quaternary ammonium chloride is used as the solvent, fusing the reagents at about 100° C.

4. A process according to claim 1, 2 or 3 wherein the quaternary ammonium chloride is methyltriethylammonium or tetraethylammonium chloride.

5. A process according to claim 1 wherein the chlorination is with phosphorus oxychloride and a weak tertiary amine base hydrochloride.

6. A process according to claim 5 wherein the weak base is N,N-dimethylaniline or diethylaniline.

* * * * *